United States Patent
Nadershahi et al.

(10) Patent No.: US 9,907,544 B2
(45) Date of Patent: Mar. 6, 2018

(54) MINIMALLY OBSTRUCTIVE RETRACTOR FOR VAGINAL REPAIRS

(71) Applicant: Alfred E. Mann Institute for Biomedical Engineering at the University of Southern California, Los Angeles, CA (US)

(72) Inventors: Afshin Nadershahi, Northridge, CA (US); Krishna Mohith Jetti, Oakbrook Terrace, IL (US); Sudeep Deshpande, Los Angeles, CA (US)

(73) Assignee: PROA MEDICAL, INC., Redondo Beach, CA (US)

( * ) Notice: Subject to any disclaimer, the term of this patent is extended or adjusted under 35 U.S.C. 154(b) by 425 days.

(21) Appl. No.: 14/468,167

(22) Filed: Aug. 25, 2014

(65) Prior Publication Data

US 2014/0364698 A1 Dec. 11, 2014

Related U.S. Application Data

(63) Continuation-in-part of application No. 13/248,928, filed on Sep. 29, 2011, now Pat. No. 9,050,048.
(Continued)

(51) Int. Cl.
*A61B 17/02* (2006.01)
*A61B 1/32* (2006.01)
(Continued)

(52) U.S. Cl.
CPC ............... *A61B 17/02* (2013.01); *A61B 1/32* (2013.01); *A61B 17/0218* (2013.01);
(Continued)

(58) Field of Classification Search
CPC .......... A61B 1/303; A61B 1/32; A61B 17/02; A61B 17/0206; A61B 17/0218;
(Continued)

(56) References Cited

U.S. PATENT DOCUMENTS 55,511 A * 6/1866 Leutz ..................... A61B 1/32
600/213
361,087 A 4/1887 Schenck
(Continued)

FOREIGN PATENT DOCUMENTS

CN 1863479 A 11/2006
CN 2836839 Y 11/2006
(Continued)

OTHER PUBLICATIONS

Communication Pursuant to Article 94(3) EPC, dated Jun. 15, 2015, for European Application 11831346.9, entitled "Minimally Obstructive Retractor," European regional phase of PCT/US2011/054064, PCT counterpart to U.S. Appl. No. 13/248,928, now U.S. Pat. No. 9,050,048 B2.
(Continued)

*Primary Examiner* — Eric S Gibson
(74) *Attorney, Agent, or Firm* — McDermott Will & Emery

(57) ABSTRACT

This application presents minimally-obstructive and structurally-adjustable retractors for vaginal repairs, which afford an open work area of desirable size and enhanced visualization for a surgeon about the perineum and the posterior vaginal wall of the patient. The retractors may be lightweight and compact, and also configured and dimensioned to minimize slippage during use. The retractors may have occluders that may partially or substantially block or absorb fluids, for example, from or around the cervix. The retractors may incorporate built-in light sources. The retractors may retract the engorged labia of the postpartum patient as well as the vaginal walls. The retractor may also be used as a speculum.

41 Claims, 15 Drawing Sheets

Related U.S. Application Data

(60) Provisional application No. 61/871,222, filed on Aug. 28, 2013, provisional application No. 61/871,229, filed on Aug. 28, 2013, provisional application No. 61/871,233, filed on Aug. 28, 2013.

(51) Int. Cl.
*A61B 17/42* (2006.01)
*A61B 17/00* (2006.01)
*A61B 17/12* (2006.01)
*A61B 90/30* (2016.01)

(52) U.S. Cl.
CPC .. *A61B 17/12099* (2013.01); *A61B 17/12136* (2013.01); *A61B 17/42* (2013.01); *A61B 17/12045* (2013.01); *A61B 2017/00407* (2013.01); *A61B 2017/00557* (2013.01); *A61B 2017/00849* (2013.01); *A61B 2090/309* (2016.02)

(58) Field of Classification Search
CPC .... A61B 2017/0212; A61B 2017/0225; A61B 2017/0237; A61B 2017/0243
USPC ................................. 600/201–246
See application file for complete search history.

(56) References Cited

U.S. PATENT DOCUMENTS

| | | | | |
|---|---|---|---|---|
| 424,140 A * | 3/1890 | Shuford | A61B 1/32 | 600/219 |
| 469,351 A * | 2/1892 | Sparenburg | A61B 1/32 | 600/224 |
| 583,932 A * | 6/1897 | Penderson | A61B 17/0206 | 600/219 |
| 639,444 A | 12/1899 | Scheerer | | |
| 688,935 A * | 12/1901 | Crane | A61B 1/32 | 600/223 |
| 761,821 A | 6/1904 | Clark et al. | | |
| 786,457 A | 4/1905 | McGinnis | | |
| 810,675 A * | 1/1906 | Richter | A61B 17/0206 | 600/217 |
| 847,542 A * | 3/1907 | Barber | A61B 1/32 | 600/225 |
| 977,489 A * | 12/1910 | Unruh | A61B 1/32 | 600/224 |
| 1,014,799 A | 1/1912 | Arthur | | |
| 2,012,597 A * | 8/1935 | Cameron | A61B 1/227 | 600/219 |
| 2,374,863 A * | 5/1945 | Guttmann | A61B 1/32 | 600/224 |
| 3,176,682 A | 4/1965 | Wexler | | |
| 3,736,919 A * | 6/1973 | Cotey | A61B 1/32 | 600/220 |
| 3,745,992 A * | 7/1973 | Poirier | A61B 1/32 | 600/220 |
| 3,774,596 A | 11/1973 | Cook | | |
| 3,789,829 A * | 2/1974 | Hasson | A61N 5/1016 | 600/221 |
| 3,796,214 A | 3/1974 | Davis | | |
| 4,130,113 A * | 12/1978 | Graham | A61B 17/0293 | 600/224 |
| 4,156,424 A * | 5/1979 | Burgin | A61B 1/32 | 600/212 |
| 4,263,898 A * | 4/1981 | Wannag | A61B 1/32 | 600/220 |
| 4,300,541 A * | 11/1981 | Burgin | A61B 1/32 | 600/213 |
| 4,447,227 A * | 5/1984 | Kotsanis | A61B 17/0218 | 604/908 |
| 4,754,746 A * | 7/1988 | Cox | A61B 17/0206 | 600/210 |
| 4,807,600 A * | 2/1989 | Hayes | A61B 1/32 | 600/203 |
| 1,971,036 A | 11/1990 | Collins | | |
| 5,081,983 A * | 1/1992 | Villalta | A61B 17/02 | 600/224 |
| 5,183,032 A * | 2/1993 | Villalta | A61B 17/02 | 600/214 |
| 5,209,754 A * | 5/1993 | Ahluwalia | A61B 17/0218 | 600/207 |
| 5,439,476 A * | 8/1995 | Frantzides | A61B 17/0218 | 600/207 |
| 5,465,709 A * | 11/1995 | Dickie | A61B 1/32 | 600/223 |
| 5,509,893 A * | 4/1996 | Fracas | A61B 1/32 | 600/184 |
| RE35,312 E * | 8/1996 | Christoudias | A61B 17/00234 | 600/207 |
| 5,613,950 A * | 3/1997 | Yoon | A61B 17/00234 | 600/225 |
| 5,626,129 A * | 5/1997 | Klimm | A61M 16/0051 | 128/202.22 |
| 5,643,285 A * | 7/1997 | Rowden | A61B 17/4241 | 606/119 |
| 5,785,648 A * | 7/1998 | Min | A61B 1/32 | 600/206 |
| 5,792,044 A * | 8/1998 | Foley | A61B 17/02 | 600/102 |
| 5,800,394 A * | 9/1998 | Yoon | A61B 17/00234 | 600/207 |
| 5,868,668 A * | 2/1999 | Weiss | A61B 1/32 | 600/221 |
| 5,894,843 A * | 4/1999 | Benetti | A61B 17/00234 | 128/898 |
| 5,931,777 A * | 8/1999 | Sava | A61B 17/02 | 600/210 |
| 5,944,736 A * | 8/1999 | Taylor | A61B 17/0206 | 600/201 |
| 5,984,350 A * | 11/1999 | Hagan | B60R 21/01 | 280/733 |
| 6,024,696 A * | 2/2000 | Hoftman | A61B 1/303 | 600/224 |
| 6,024,697 A * | 2/2000 | Pisarik | A61B 1/32 | 600/214 |
| 6,048,308 A * | 4/2000 | Strong | A61B 1/303 | 600/205 |
| 6,096,046 A * | 8/2000 | Weiss | A61B 17/0206 | 600/210 |
| 6,196,969 B1 * | 3/2001 | Bester | A61B 17/0206 | 600/219 |
| 6,265,984 B1 * | 7/2001 | Molinaroli | A63H 33/40 | 340/815.4 |
| 6,280,379 B1 * | 8/2001 | Resnick | A61B 1/32 | 600/220 |
| 6,302,842 B1 | 10/2001 | Auerbach et al. | | |
| 6,312,377 B1 * | 11/2001 | Segermark | A61B 17/02 | 600/201 |
| 6,346,074 B1 * | 2/2002 | Roth | A61B 17/00234 | 600/121 |
| 6,364,832 B1 | 4/2002 | Propp | | |
| 6,395,012 B1 * | 5/2002 | Yoon | A61B 17/00234 | 606/193 |
| 6,416,467 B1 * | 7/2002 | McMillin | A61B 1/32 | 600/220 |
| 6,432,048 B1 | 8/2002 | Francois | | |
| 6,450,952 B1 * | 9/2002 | Rioux | A61B 1/0669 | 600/219 |
| 6,492,963 B1 * | 12/2002 | Hoch | B62J 6/20 | 340/432 |
| 6,589,168 B2 * | 7/2003 | Thompson | A61B 1/32 | 600/220 |
| 6,595,917 B2 * | 7/2003 | Nieto | A61B 1/32 | 600/220 |
| 6,599,292 B1 * | 7/2003 | Ray | A61B 17/025 | 600/219 |
| 6,740,031 B2 * | 5/2004 | Davidson | A61B 17/42 | 600/219 |

(56) References Cited

U.S. PATENT DOCUMENTS

| | | | |
|---|---|---|---|
| 7,060,029 B1* | 6/2006 | Hajianpour | A61B 1/303 600/184 |
| 7,070,561 B1 | 7/2006 | Ansari | |
| 7,141,015 B2 | 11/2006 | Ruane | |
| 7,144,368 B2* | 12/2006 | Larson | A61B 1/32 600/215 |
| 7,175,594 B2* | 2/2007 | Foulkes | A61B 1/00094 600/219 |
| 7,248,038 B2* | 7/2007 | Wilhelmy | G01D 5/2013 324/207.2 |
| 7,481,766 B2 | 1/2009 | Lee et al. | |
| 7,594,888 B2* | 9/2009 | Raymond | A61B 17/3439 600/215 |
| 7,658,712 B2 | 2/2010 | Klassen et al. | |
| 7,837,580 B2* | 11/2010 | Huang | F42B 6/06 473/570 |
| 7,901,409 B2* | 3/2011 | Canaveral | A61B 17/8858 600/222 |
| 7,988,625 B2* | 8/2011 | Abdelgany | A61B 17/02 600/220 |
| 8,409,087 B2* | 4/2013 | Ames | A61B 17/025 600/210 |
| 8,409,091 B2* | 4/2013 | Blain | A61B 17/0206 600/201 |
| 8,449,568 B2* | 5/2013 | Nevyas-Wallace | A61F 9/007 600/219 |
| 8,460,187 B2* | 6/2013 | Bouquet | A61M 29/00 600/222 |
| 8,517,935 B2* | 8/2013 | Marchek | A61B 17/02 600/233 |
| 8,523,767 B2* | 9/2013 | DeRidder | A61B 1/32 600/208 |
| 8,535,320 B2* | 9/2013 | Woolley | A61B 17/0206 600/210 |
| 8,550,994 B2* | 10/2013 | Miles | A61B 17/02 600/202 |
| 8,568,306 B2* | 10/2013 | Hardenbrook | A61B 17/0206 600/210 |
| 8,574,155 B2* | 11/2013 | O'Prey | A61B 17/0206 600/228 |
| 8,591,432 B2* | 11/2013 | Pimenta | A61B 1/32 600/554 |
| 8,636,655 B1* | 1/2014 | Childs | A61B 17/0206 600/219 |
| 8,696,561 B2* | 4/2014 | Fenster | A61B 1/303 600/221 |
| 8,734,337 B2* | 5/2014 | Deitch | A61B 1/32 600/220 |
| 8,747,308 B2* | 6/2014 | Muzzammel | A61B 1/32 600/220 |
| 8,770,200 B2* | 7/2014 | Ahluwalia | A61F 6/06 128/830 |
| 8,777,849 B2* | 7/2014 | Haig | A61B 17/0206 600/206 |
| 8,795,167 B2* | 8/2014 | Ainsworth | A61B 17/0642 600/222 |
| 8,814,789 B2* | 8/2014 | Deitch | A61B 1/32 600/220 |
| 8,827,900 B1* | 9/2014 | Pimenta | A61B 17/0206 600/202 |
| 8,951,226 B2* | 2/2015 | Hameed | A61B 1/00082 128/200.24 |
| 9,050,048 B2 | 6/2015 | Nadershahi et al. | |
| 9,050,058 B2 | 6/2015 | Nadershahi et al. | |
| 2002/0156350 A1 | 10/2002 | Nieto | |
| 2003/0171656 A1 | 9/2003 | Foulkes | |
| 2003/0225313 A1 | 12/2003 | Borodulin et al. | |
| 2004/0002629 A1* | 1/2004 | Branch | A61B 17/0206 600/210 |
| 2004/0116777 A1* | 6/2004 | Larson | A61B 17/02 600/210 |
| 2005/0080320 A1* | 4/2005 | Lee | A61B 17/02 600/214 |
| 2005/0113644 A1* | 5/2005 | Obenchain | A61B 17/0206 600/222 |
| 2005/0215862 A1 | 9/2005 | Larson et al. | |
| 2005/0234304 A1* | 10/2005 | Dewey | A61B 17/0206 600/210 |
| 2006/0004261 A1* | 1/2006 | Douglas | A61B 17/0218 600/210 |
| 2006/0074278 A1* | 4/2006 | Petit | A61B 17/0293 600/224 |
| 2006/0155170 A1* | 7/2006 | Hanson | A61B 17/02 600/201 |
| 2006/0235279 A1* | 10/2006 | Hawkes | A61B 1/32 600/222 |
| 2007/0027364 A1* | 2/2007 | Schwer | A61B 17/0206 600/219 |
| 2007/0208227 A1* | 9/2007 | Smith | A61B 1/313 600/219 |
| 2007/0219416 A1* | 9/2007 | Perez-Cruet | A61B 17/02 600/219 |
| 2008/0058604 A1* | 3/2008 | Sorensen | A61B 1/32 600/208 |
| 2008/0091080 A1* | 4/2008 | Leahy | A61B 17/3423 600/207 |
| 2008/0214898 A1* | 9/2008 | Warren | A61B 17/02 600/210 |
| 2008/0228038 A1 | 9/2008 | McMahon et al. | |
| 2008/0245371 A1 | 10/2008 | Gruber | |
| 2008/0269565 A1* | 10/2008 | McMahon | A61B 1/00105 600/203 |
| 2008/0306345 A1* | 12/2008 | Balas | A61B 1/303 600/214 |
| 2009/0062042 A1* | 3/2009 | Huang | F42B 6/06 473/578 |
| 2009/0076334 A1* | 3/2009 | Chen | A61B 1/303 600/223 |
| 2009/0099422 A1* | 4/2009 | George | A61B 1/32 600/214 |
| 2009/0198108 A1* | 8/2009 | Chen | A61B 1/00103 600/220 |
| 2009/0259109 A1* | 10/2009 | Bucefari | A61B 17/02 600/219 |
| 2009/0265941 A1* | 10/2009 | Kurrus | A61M 25/0009 30/186 |
| 2009/0318914 A1 | 12/2009 | Utley et al. | |
| 2009/0326331 A1* | 12/2009 | Rosen | A61B 1/303 600/224 |
| 2010/0069947 A1* | 3/2010 | Sholev | A61B 17/00234 606/192 |
| 2010/0168523 A1* | 7/2010 | Ducharme | A61B 17/0218 600/207 |
| 2010/0191067 A1* | 7/2010 | Chen | A61B 1/00052 600/245 |
| 2010/0210901 A1* | 8/2010 | Makower | A61B 17/24 600/104 |
| 2010/0217091 A1* | 8/2010 | Sullivan | A61B 1/32 600/222 |
| 2010/0234689 A1* | 9/2010 | Wagner | A61B 17/0206 600/210 |
| 2010/0271010 A1* | 10/2010 | Stevens | B23Q 17/003 324/207.2 |
| 2010/0305406 A1* | 12/2010 | Braun | H01C 7/006 600/202 |
| 2011/0021879 A1* | 1/2011 | Hart | A61B 17/0293 600/207 |
| 2011/0201894 A1* | 8/2011 | O'Prey | A61B 17/0293 600/219 |
| 2011/0224742 A1* | 9/2011 | Weisel | A61B 17/0218 606/86 R |
| 2012/0083658 A1* | 4/2012 | Hahn | A61B 1/32 600/205 |
| 2012/0108907 A1* | 5/2012 | Fitipaldi | A61B 1/32 600/223 |
| 2012/0232352 A1* | 9/2012 | Lin | A61B 1/32 600/220 |

(56) References Cited

U.S. PATENT DOCUMENTS

| | | | |
|---|---|---|---|
| 2013/0006061 A1* | 1/2013 | Alexander | A61B 1/32 600/235 |
| 2013/0023914 A1 | 1/2013 | Truong et al. | |
| 2013/0041229 A2 | 2/2013 | Hahn et al. | |
| 2013/0053863 A1* | 2/2013 | Juravic | A61B 1/303 606/119 |
| 2013/0103103 A1* | 4/2013 | Mire | A61B 1/32 606/86 A |
| 2013/0190575 A1* | 7/2013 | Mast | A61B 17/7079 600/215 |
| 2013/0274561 A1* | 10/2013 | Deitch | A61B 17/42 600/219 |
| 2014/0309500 A1* | 10/2014 | Thompson | A61B 17/0206 600/219 |
| 2014/0364695 A1 | 12/2014 | Nadershahi et al. | |
| 2014/0364698 A1* | 12/2014 | Nadershahi | A61B 1/32 600/215 |
| 2016/0045220 A1* | 2/2016 | Wachli | A61B 17/3423 600/204 |
| 2016/0270819 A1* | 9/2016 | Ahluwalia | A61B 17/4241 |

FOREIGN PATENT DOCUMENTS

| | | | |
|---|---|---|---|
| CN | 101287404 A | 10/2008 | |
| CN | 101433452 A | 5/2009 | |
| CN | 101657164 A | 2/2010 | |
| CN | 201500147 U | 6/2010 | |
| CN | 102639182 A | 8/2012 | |
| DE | 19828099 A1 | 12/1999 | |
| SU | 167005 A1 | 1/1965 | |
| SU | 1509048 A1 | 9/1989 | |
| WO | 2002054961 A1 | 7/2002 | |
| WO | 2004002322 A1 | 1/2004 | |
| WO | 2004098416 A2 | 11/2004 | |
| WO | 2009099543 A2 | 11/2004 | |
| WO | 2005016131 A1 | 2/2005 | |
| WO | 2006107878 A2 | 10/2006 | |
| WO | WO2007075903 A2 | 7/2007 | |
| WO | WO 2007075903 A2 * | 7/2007 | A61B 7/0218 |
| WO | 2011/047066 A2 | 4/2011 | |
| WO | 2012047725 A1 | 4/2012 | |

OTHER PUBLICATIONS

Office Action, dated Jul. 28, 2015, for Chinese Application No. 201180047230.8, entitled "Minimally Obstructive Retractor," Chinese national phase of PCT/US2011/054064, PCT counterpart to U.S. Appl. No. 13/248,928, now U.S. Pat. No. 9,050,048 B2.
Office Action, dated Jul. 30, 2015, for Mexican Application No. MX/a/2013/003598, entitled "Minimally Obstructive Retractor" (memorandum with translation only) for Mexican national phase of PCT/US2011/054064, PCT counterpart to U.S. Appl. No. 13/248,928, now U.S. Pat. No. 9,050,048 B2.
International Search Report and Written Opinion of the US International Searching Authority (ISA/US), dated Dec. 18, 2014, for PCT Application No. PCT/US2014/052573, entitled "Minimally Obstructive Retractor for Vaginal Repairs," filed Aug. 25, 2014.
International Search Report and Written Opinion of the US International Searching Authority (ISA/US), dated Dec. 30, 2014, for PCT Application No. PCT/US2014/052574, entitled "Speculum for Obstetrical and Gynecological Exams and Related Procedures," filed Aug. 25, 2014.
Office Action, dated Jan. 12, 2015, for Chinese Application No. 201180047230.8, entitled "Minimally Obstructive Retractor", Chinese national phase of PCT/US2011/054064, PCT counterpart to U.S. Appl. No. 13/248,928.
US Patent Office. 2015. Notice of Allowance, dated Feb. 28, 2015, for U.S. Appl. No. 13/248,928, entitled "Minimally Obstructive Retractor."
Cooper Surgical, Inc. 2009. Guardian Vaginal Retractor, two pages.
Frankman et al., 2009. Episiotomy in the United States: has anything changed?, Am J Obstet Gyncol, vol. 200, 573.e1-573.e7.
Leeman et al. 2003. Repair of Obstetric Perineal Lacerations, American Family Physician, pp. 1586-1590, vol. 68, No. 8.
Weber et al. 2002. Episiotomy Use in the United States, 1979-1997, Obstetrics & Gynecology, pp. 1177-1182, vol. 100, No. 6.
International Search Report and Written Opinion of International Searching Authority for PCT Application No. PCT/US2011/054064, dated Sep. 29, 2011, entitled "Minimally Obstructive Retractor," published Apr. 12, 2012 as WO 2012/047725 A1.
Official Action, dated May 15, 2014, from the Patent Office of the Russian Federation, for counterpart Russian Application No. 2013119383, entitled "Minimally Obstructive Retractor," national phase filing in Russia based on WO 2012/047725 (with translation and redacted cover sheet provided by Russian counsel, showing receipt date).
Extended European Search Report, dated Jul. 23, 2014, from the European Patent Office, for European Application No. 11831346.9, entitled "Minimally Obstructive Retractor," European Regional Phase filing based on WO 2012/047725.
U.S. Appl. No. 14/468,210, filed Aug. 25, 2014, entitled "Speculum for Obstetrical and Gynecological Exams and Related Procedures," Afshin Nadershahi et al., inventors.
Office Action dated Nov. 10, 2014 for U.S. Appl. No. 13/248,928, filed Sep. 29, 2011, Ricardo Hahn et al., inventors, entitled "Minimally Obstructive Retractor."
Communication Pursuant to Article 94(3) EPC, dated May 2, 2016, for European Application 11831346.9, entitled "Minimally Obstructive Retractor," European regional phase of PCT/US2011/054064, PCT counterpart to U.S. Pat. No. 13/248,928, now U.S. Pat. No. 9,050,048 B2.
Office Action dated Mar. 2, 2017, which issued in U.S. Appl. No. 14/468,210.
Extended European Search Report from European Application No. 14839098.2, dated Feb. 28, 2017.
Extended European Search Report from European Application No. 14840847.9, dated Feb. 21, 2017.
Chinese Office Action from Chinese Patent Application No. 201480047470.1, dated Apr. 13, 2017.
Chinese Office Action from Chinese Patent Application No. 201480047631.7, dated Sep. 22, 2017, 18 pages.

* cited by examiner

US 9,907,544 B2

MINIMALLY OBSTRUCTIVE RETRACTOR FOR VAGINAL REPAIRS

CROSS-REFERENCE TO RELATED APPLICATIONS

This application is based upon and claims priority to U.S. Provisional Patent Application Ser. No. 61/871,222, filed Aug. 28, 2013, entitled "Retractor for Vaginal Repairs"; U.S. Provisional Patent Application Ser. No. 61/871,229, filed Aug. 28, 2013, entitled "Speculum for Colposcopy"; and U.S. Provisional Patent Application Ser. No. 61/871,233, filed Aug. 28, 2013, entitled "Retractor for Surgical Incisions." This application is also a continuation-in-part of U.S. patent application Ser. No. 13/248,928, filed Sep. 29, 2011, entitled "Minimally Obstructive Retractor." The entire contents of these applications are incorporated herein by reference.

TECHNICAL FIELD

This disclosure relates generally to medical surgical instruments, particularly structurally-adjustable retractors and speculums for gynecological operations and examinations.

DESCRIPTION OF RELATED ART

Devices which have been proposed for the purpose of vaginal examination and gynecological surgical procedures may not be entirely satisfactory for a variety of reasons. In many cases, they may obstruct the vision of the deep internal parts of the vaginal cavity that they are intended to expose. They may also constrain the movement of the physicians' hands and reduce the open work area for the surgeon. They may also fail to prevent fluids from obscuring inspection and obstructing the work area for the surgeon. This often reduces the efficiency and effectiveness of vaginal examinations and surgical procedures.

Furthermore, typically the vagina walls, the perineum (which is the area of tissue between the vagina and the anus), and the anus are torn during vaginal delivery. Natural perineal tears are classified by their severity. First-degree tears involve tearing only the skin. Second-degree tears involve tearing muscle. Third-degree tears involve tearing the external anal sphincter muscle. Fourth-degree tears further involve tearing the rectal mucosa. When fourth-degree tears occur, the mother may require post-birth surgery to stitch up the torn tissue, often under general anesthetic.

Sometimes the perineum is purposely cut by a doctor performing an episiotomy, which is an incision into the perineum to enlarge the size of the vaginal opening. An episiotomy is similar to a first or second-degree natural tear.

All of the above tearing or incisions usually require post-delivery operations to stitch up the area. Stitching fourth-degree tears is particularly difficult using known specula given that fourth-degree tears typically extend from the vagina wall all the way to the rectum. Such surgery is extremely difficult due to the flaccid nature of the surrounding tissue which exists immediately after birth.

Episiotomy retractors for retracting friable postpartum vaginal tissue to facilitate repair of the episiotomy or vaginal laceration are known. The primary function of the retractor is to provide an open work area for the surgeon about the perineum and posterior vaginal wall of the patient so that the surgeon can conveniently and safely approximate and suture the tissue planes to complete repair.

The known episiotomy retractors may not be entirely satisfactory in use. Existing retractors may not permit access to the area in which the stitching is required and furthermore may tend to interfere with the surgeons ability to make the stitches in the first place.

Most importantly, conventional retractors may fail to provide sufficient open work area for the surgeon about the perineum and the posterior vaginal wall of the patient. During the delivery process the labia of the patient may become engorged with blood and thus may tends to interfere with visualization of the desired work area by the surgeon. Additionally, fluids may obscure inspection and obstruct the work area; the surgeon often must place gauze above the suturing site to absorb and block excess fluids from obscuring the work area.

Furthermore, conventional retractors often include scissor arms or other elongated portions for gripping and leverage. However, these elements may increase the size and cost of the devices, and can constrain the movement of the physicians' hands and reduce the open work area for the surgeon.

SUMMARY

This disclosure relates generally to medical surgical instruments, particularly structurally-adjustable retractors and speculums for gynecological operations and examinations.

This disclosure particularly relates to a system comprising a retractor ("retractor") having a proximal end and a distal end, and an exterior surface and an interior surface that may comprise a central body portion, at least two wings, one hinge that affixes each wing to the central body portion; and an occluder to occlude bodily fluids. The occluder may be an occluder that may be attached to a component of the system. The occluder may be an occluder that may occlude bodily fluid from entering into an area of tissue surrounded by the at least two spread wings. The occluder may be an occluder that may occlude bodily fluid from entering into an area of a vagina surrounded by the at least two spread wings.

The occluder may occlude the bodily fluids by forming a barrier that is partially impermeable to the bodily fluid. The occluder may occlude the bodily fluid by forming a barrier that is substantially impermeable to the bodily fluids. The occluder may comprise a material that absorbs bodily fluid. The occluder comprises a porous material. The porous material may comprise gauze, foam, or combinations thereof.

The occluder may be movable with respect to the central body portion.

The retractor may further comprise a distal tip and wherein the occluder may be permanently attached to the distal tip.

The occluder may comprise an inflatable article. The inflatable article may comprise only one balloon. That is, the inflatable article may not have more than one balloon. The inflatable article may also comprise only two balloons. That is, the inflatable article may not have more than two balloons. The inflatable article may be inflatable by a fluid.

The occluder may comprise a balloon tamponade system that may be temporarily attachable to the retractor. The occluder may comprise a single balloon tamponade system that may be temporarily attachable to the retractor. The occluder may comprise a double balloon tamponade system that may be temporarily attachable to the retractor, and wherein the one balloon of the double balloon tamponade system may function as a uterine tamponade balloon, and wherein the other balloon of the double balloon tamponade system may function as a vaginal tamponade balloon.

The system may further comprise a secondary device that may be temporarily attachable to the retractor. The retractor may further comprise a docking port to securely attach the secondary device to the retractor.

The occluder may comprise a flap. The flap may be foldable.

The retractor may have only two wings and only one central body portion. That is, the retractor may not have more than two wings and may not have more than one central body portion.

The occluder may comprise a porous material, and wherein the occluder may be movable with respect to the central body portion.

The system may further comprise a secondary device that may be temporarily attachable to the retractor, and wherein the retractor may further comprise a docking port to securely attach the secondary device to the retractor.

The instant disclosure also relates to a method of using the retractor or the system. In one example, the method of using the retractor or the system may comprise comprising inserting the retractor into a vagina. In another example, inserting the retractor may occlude the cervix in a way that reduces the flow of the bodily fluids into the vagina.

In one example of the method, the occluder may be movable with respect to the central body portion, and wherein the method may further comprise moving the occluder towards the cervix after inserting the retractor to reduce the flow of the bodily fluids into the vagina.

In another example, the method may further comprise repositioning the retractor after inserting the retractor by rotating the retractor within the vagina. Yet in another example, the method may further comprise repositioning the retractor after inserting the retractor by removing the retractor from the vagina, and then re-inserting the retractor within the vagina.

The method may also further comprise spreading the at least two wings apart while in the vagina. In another example, the method may further comprise closing the wings after spreading the wings and then removing the retractor from the vagina.

In another example of the method of claim 23, the occluder may further comprise a balloon tamponade system, wherein the balloon tamponade system may further comprise a catheter, wherein the retractor may further comprise a docking port to securely and detachably attach the balloon tamponade system to the retractor, and wherein the method may further comprise attaching the balloon tamponade system to the retractor, and then inserting the retractor into the vagina.

In one exemplary method, the vagina may have a laceration having an apex deep in the vagina, and wherein the method may further comprise suturing the laceration starting at the apex of the laceration, continuing with the suturing towards the introitus of the vagina, and gradually closing the wings while continuing with the suturing.

Any combination of features and/or embodiments of the retractor and the system, and the method of their use disclosed above is within the scope of this disclosure.

It is understood that other embodiments of the devices and methods will become readily apparent to those skilled in the art from the following detailed description, wherein it is shown and described only exemplary embodiments of the devices, methods and systems by way of illustration. As will be realized, the devices, systems and systems are capable of other and different embodiments and its several details are capable of modification in various other respects, all without departing from the spirit and scope of the disclosure. Accordingly, the drawings and detailed description are to be regarded as illustrative in nature and not as restrictive.

BRIEF DESCRIPTION OF THE DRAWINGS

Aspects of the retractor are illustrated by way of example, and not by way of limitation, in the accompanying drawings.

DETAILED DESCRIPTION

Figure 1:
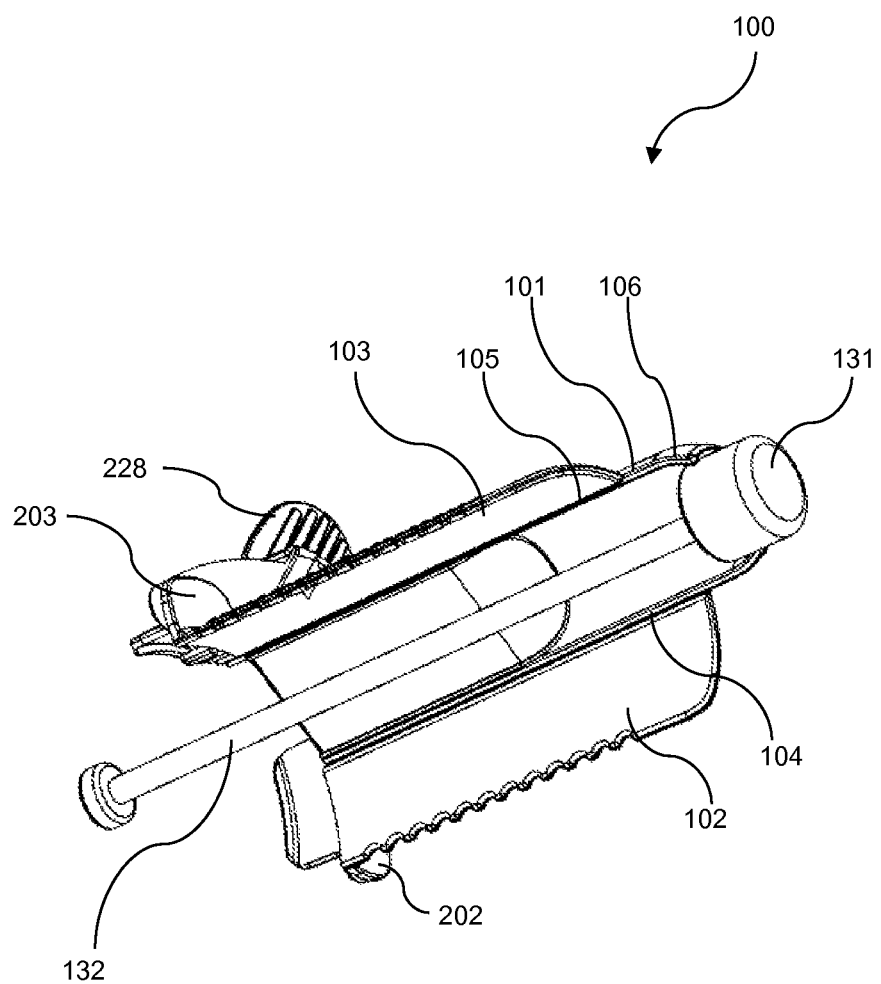
FIG. 1 is an isometric bottom view of an exemplary retractor.

The detailed description set forth below in connection with the appended drawings is intended as a description of exemplary embodiments and is not intended to represent the only embodiments in which the retractors and speculums can be practiced. The term "exemplary" used throughout this description means "serving as an example, instance, or illustration," and should not necessarily be construed as preferred or advantageous over other embodiments. The detailed description includes specific details for the purpose of providing a thorough understanding of the retractors/speculums. However, it will be apparent to those skilled in the art that the retractors/speculums may be practiced without these specific details.

This disclosure relates generally to medical surgical instruments, particularly structurally-adjustable retractors and speculums for gynecological operations and examinations. These medical devices are hereafter called "minimally obstructive retractors" or "retractors."

Previous examples of such retractors have been disclosed, for example, by Hahn et al. in the U.S. patent application Ser. No. 13/248,928, filed Sep. 29, 2011, entitled "Minimally Obstructive Retractor." The entire content of this patent application's paragraphs [0011]-[0092] and these paragraphs' accompanying figures is incorporated herein by reference.

This instant disclosure particularly relates to a system comprising a minimally obstructive retractor ("retractor"). Examples of this retractor (100) are shown in FIGS. 1-15. The retractor (100) has a proximal end and a distal end. The retractor (100) may comprise a central body portion (101), at least two wings (102,103), and at least one hinge (104, 105) affix at least one wing to the central body portion. The central body portion (101), the at least one wing (102,103), and the at least one hinge (104,105) may form a canopy.

The retractor (100) may further comprise an occluder (131). The occluder (131) may occlude bodily fluids. For example, the occluder may reduce amount of bodily fluids flowing within the vagina during medical interventions. Examples of medical interventions may be obstetric and/or gynecological procedures. The occluder (131) may partially or substantially block, and/or absorb bodily fluids. Examples of these fluids may be blood, amniotic fluid, or mixtures thereof. Such bodily fluids may originate from uterus and/or cervix. The occluder (131) may occlude or partially occlude the cervical canal or the internal opening of the cervical canal (the cervical os). The occluder may be configured such that, during the application of the retractor (100), the occluder (131) faces the cervix without touching it. The occluder (131) may also press against the cervix during the deployment of the retractor (100). The occluder (131) may help to reduce amount of fluids that may obscure inspection or interfere with a medical procedure. For example, the occluder (131) may provide tamponade effect.

The occluder (131) may have any shape that is suitable to reduce the amount of bodily fluids flowing to the vagina. In one example, the occluder may form a barrier against the flow of bodily fluids. In another example, the occluder may partially or substantially isolate an area of vagina, of which is targeted by the medical intervention, from the flow of bodily fluids.

The occluder (131) may reduce the amount of bodily fluids flowing to the vagina when the occluder is pressed against a tissue, such as a cervix. The occluder (131) may also reduce the amount of bodily fluids flowing to the vagina by forming a barrier. In one example, this barrier may be partially or substantially impermeable to the bodily fluids. An example of the partially impermeable barrier may be a gauze. In another example, this barrier may be substantially impermeable to the bodily fluids. An example of the substantially impermeable barrier is an article that has substantially small porosity or substantially small pores such that the permeation of the bodily fluids through such barrier is negligible for a particular medical intervention.

In one example, the occluder (131) may comprise a material suitable to partially or substantially block and/or absorb bodily fluids. The occluder (131) may comprise soft or flexible plastic, rubber, foam, or gauze.

The occluder (131) may be manufactured from a material suitable to absorb bodily fluids. For example, the occluder material may comprise a porous material. The porous material may be soft or flexible plastic, rubber, foam, or gauze.

Figure 2:
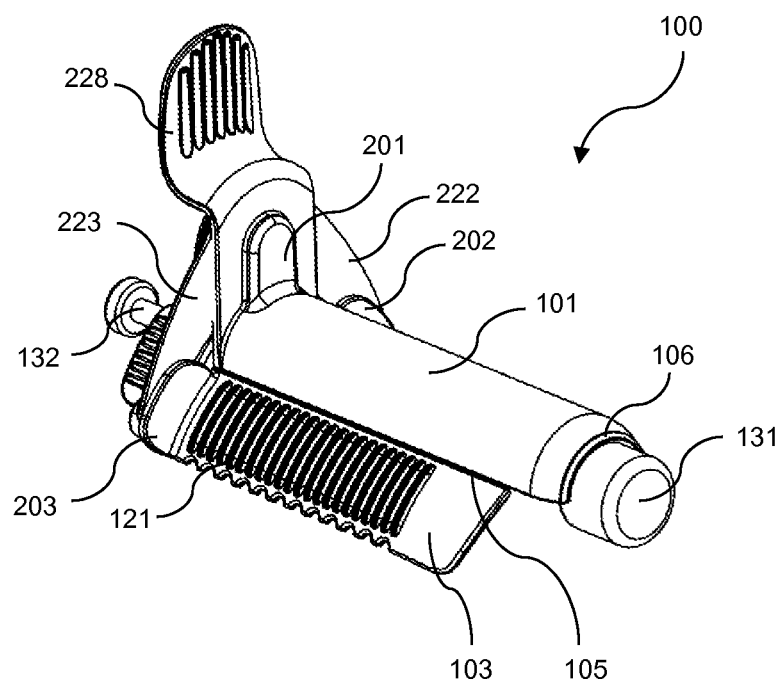
FIG. 2 is an isometric top view of the exemplary retractor of FIG. 1.
Figure 3:
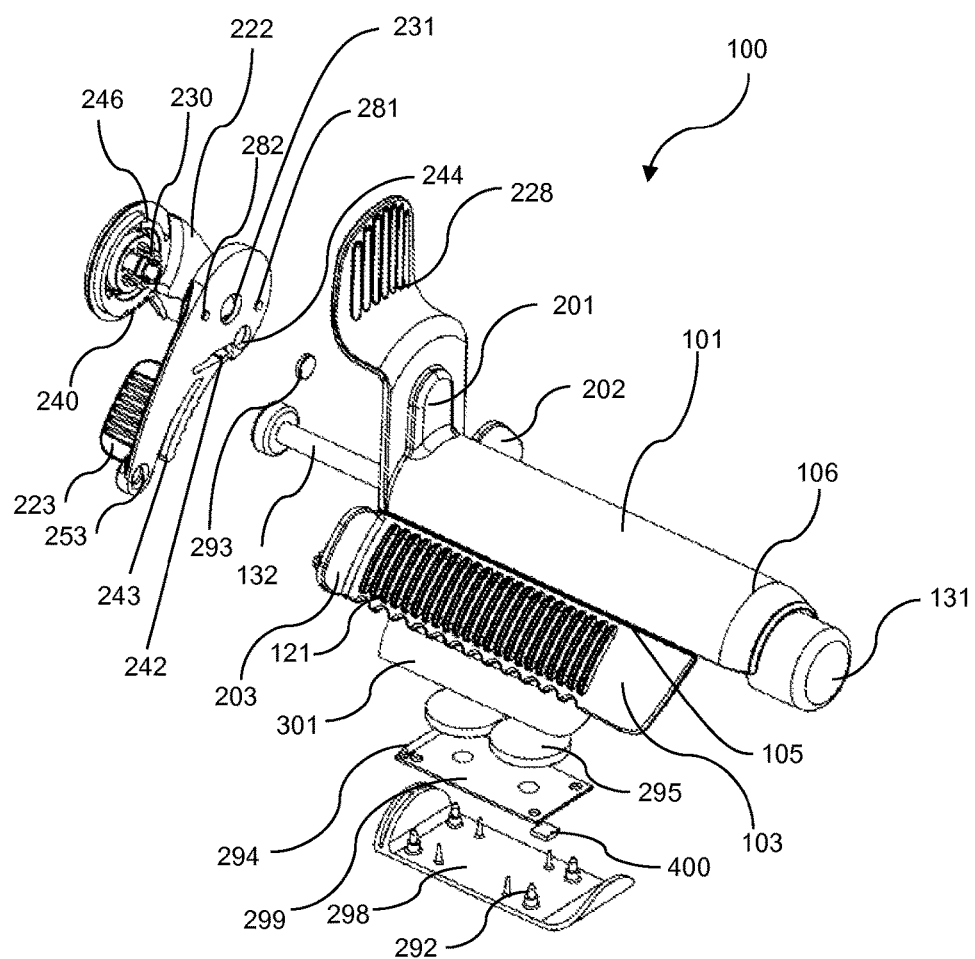
FIG. 3 is an exploded isometric view of the exemplary retractor of FIG. 1.
Figure 4:
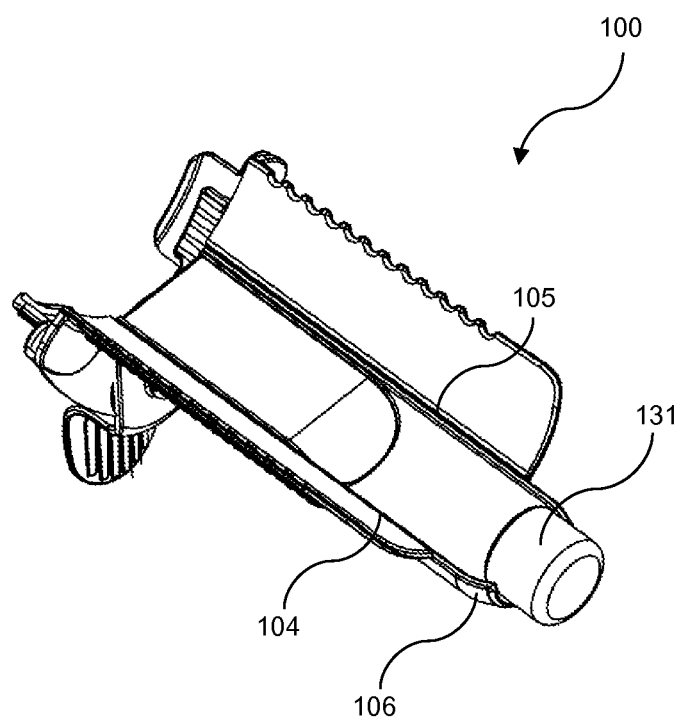
FIG. 4 is an isometric bottom view of an exemplary retractor, wherein the occluder is affixed to the distal tip.

In some examples, the occluder (131) may be attachable to and/or removable from the retractor (100) by the user, as shown in FIGS. 1-3 ("the temporarily attachable occluder").

In one example, the occluder (131) may be movable with respect to the central body portion (101). In these examples, after the retractor (100) is deployed and immobilized in the vagina, the occluder (131) may be independently moved and repositioned in the vagina to control the bodily fluids. For example, the occluder may be repositioned by using a lever, rod, switch, or other mechanisms suitable for the user control. In one example, shown in FIG. 1, the retractor may comprise a rod (132) attached to the occluder (131) by which the user can move, reposition, manipulate, and/or remove the occluder (131). The rod (132) may be attached to the occluder (131).

In other examples, the occluder (131) may be permanently attached to the retractor (100). In one example, shown in FIG. 4, the occluder (131) may be permanently attached to the retractor (131). In this example, the occluder (131) may be permanently attached to the distal tip (106).

Figure 5:
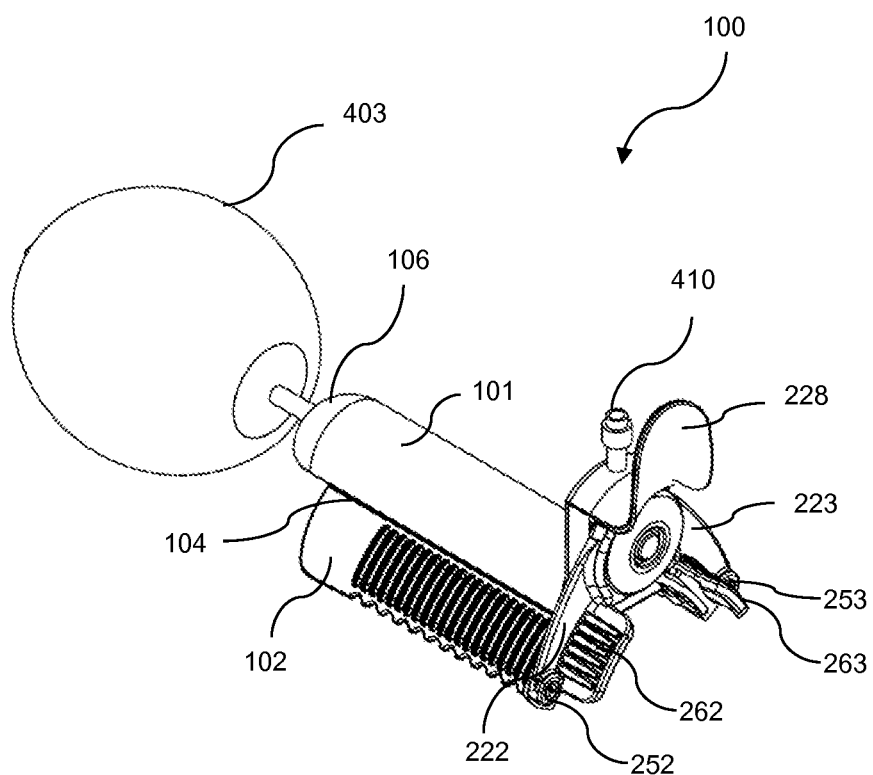
FIG. 5 is an isometric top view of an exemplary retractor comprising a balloon tamponade system.
Figure 6:
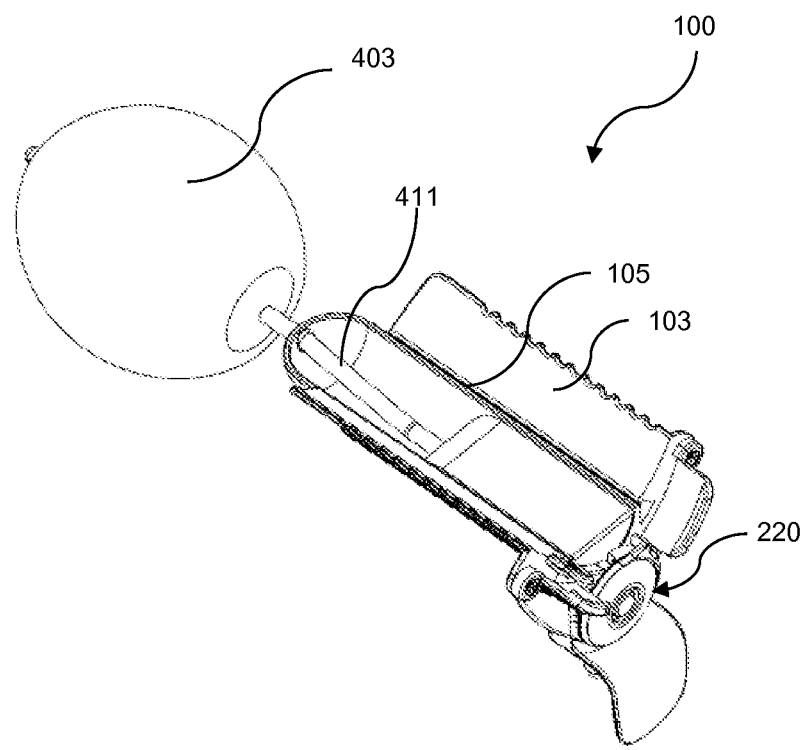
FIG. 6 is an isometric bottom view of the exemplary retractor comprising a balloon tamponade system of FIG. 5.
Figure 7:
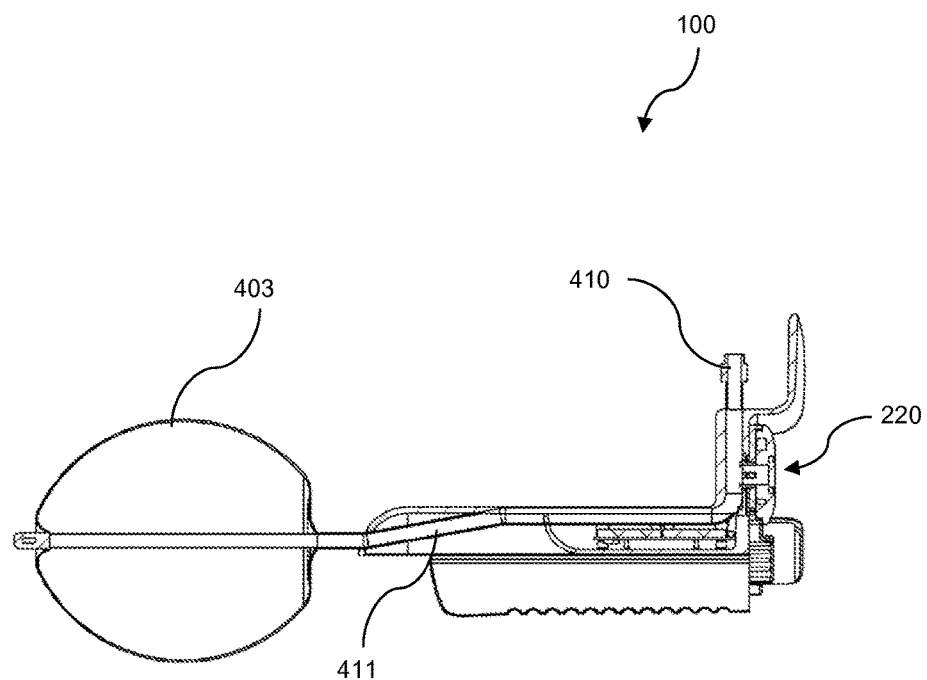
FIG. 7 is a sectional side view of the exemplary retractor comprising a balloon tamponade system of FIG. 5.
Figure 8:
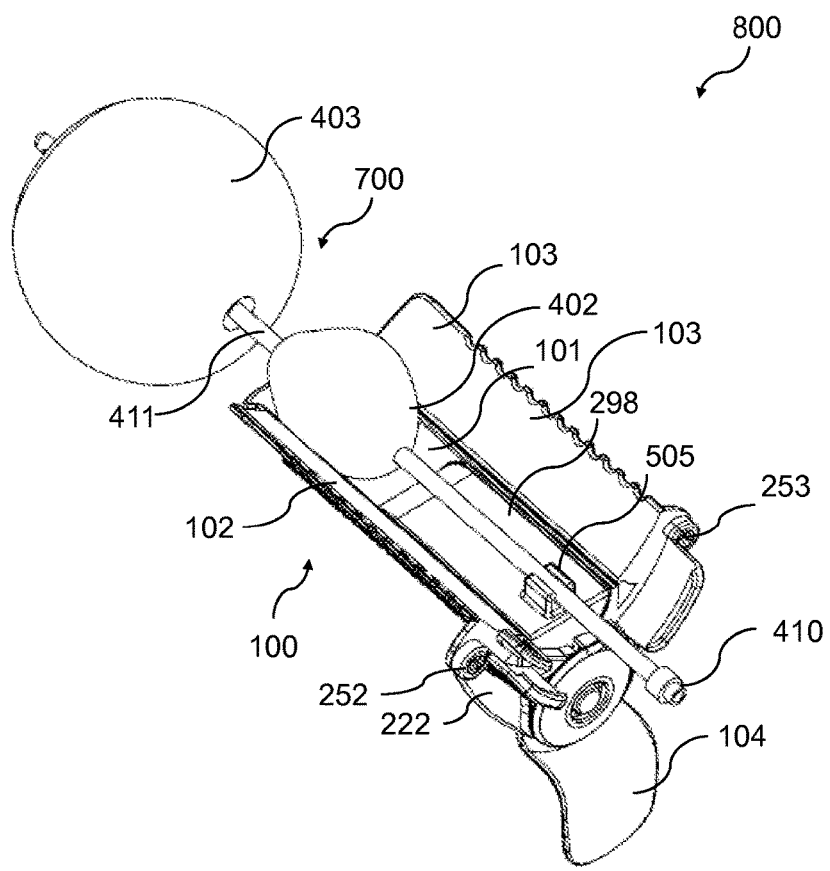
FIG. 8 is an isometric bottom view of an exemplary retractor and a balloon tamponade system attached to the exemplary retractor.
Figure 9:
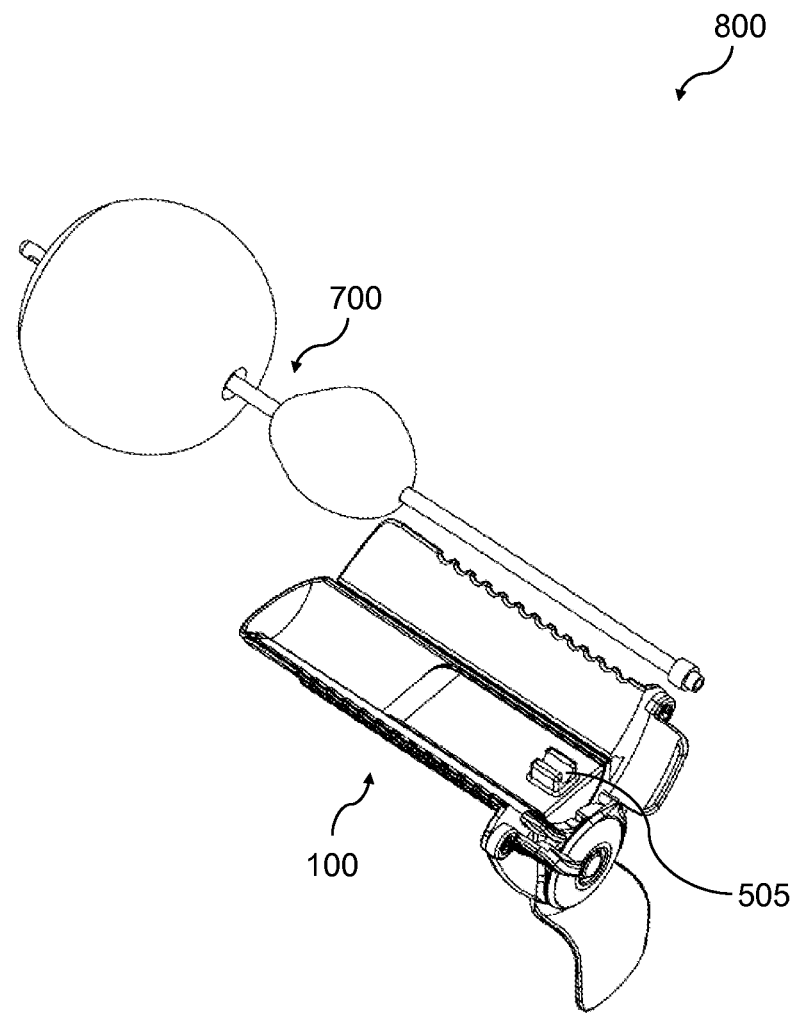
FIG. 9 is an isometric top view of the exemplary retractor and a balloon tamponade system attached to the exemplary retractor of FIG. 8.

The occluder (131) may also comprise an inflatable article. An example of the inflatable article may be a balloon (403), as shown in FIGS. 5-11. In one example, the occluder (131) may comprise only one balloon (403), as shown in FIGS. 5-7. That is, the occluder may not have more than one balloon. In another example, the occluder (131) may comprise only two balloons (402,403), as shown in FIGS. 8-11. That is, the occluder may not have more than two balloons. Yet in other example, the balloon (403) may permanently be attached to the retractor (100), as shown in FIGS. 5-7. Still in other example, the balloons (402,403) may be temporarily attached to the retractor (100), as shown in FIGS. 8-11.

The inflatable article may be inflatable by a fluid. For example, the inflatable article may be inflatable and/or deflatable by the user by using a pump and/or a valve (not shown in FIGS. 5-11). For example, the balloons (402,403) may be filled or fillable with a fluid, which may be a liquid (e.g. water) or a gas (e.g. air).

In some examples, the retractor (100) may be part of a system (800) that may or may not further comprise another independent medical device ("secondary device") (not shown in the figures). The secondary device may comprise one or more medical devices that are temporarily attachable to the retractor (100). Examples of such secondary medical device may be forceps, balloon tamponade systems, vacuum aspirators, cotton tip applicators, catheters, a secondary illumination system, and combinations thereof. For example, these secondary devices may provide medical treatment or surgical functions for obstetrical procedures.

In one example, the occluder (131) may comprise a single or double balloon tamponade system, as shown in FIGS. 5-11. An example of the single balloon tamponade system is shown in FIGS. 5-7. An example of the double balloon tamponade system (700) may comprise a vaginal tamponade balloon (402), a uterine tamponade balloon (403), and a catheter (411), as shown in FIGS. 7-11. The double balloon tamponade system may function to reduce bleeding or flow of fluid by means of closure or blockage of the space, or through application of direct pressure to the tissue. The double balloon tamponade system (700) may further comprise a balloon tamponade port (410) to attach a device, for example a pump, to inflate the balloons (402, 403). The vaginal tamponade balloon (402) may be positioned underneath the retractor's (100) canopy, whereas the uterine tamponade balloon (403) may be positioned beyond the distal end of the retractor (100). The retractor (100) may hold the catheter (411) in such a position that its proximal tip is held in a position that is easily accessible yet non-obstructive. In this example of the system, the retractor (100) and the secondary device (700) may synergistically work by providing improved visualization and access to the vaginal walls and/or perineum while reducing the flow of fluids into the site of inspection or repair.

In one example, the retractor (100) may further comprise a docking port to securely attach the secondary device (700) to the retractor (100). The docking port may temporarily hold the secondary device against the retractor (100) such that the secondary device does not obstruct the user from performing inspection or procedures upon the vaginal walls or surrounding anatomic structures. Examples of the docking ports may be clips, fasteners, loops, hooks, adhesive pads, and combinations thereof. In one example, the occluder (131) may comprise the double balloon tamponade system (700). In this example, the catheter (411) of the double balloon tamponade system (700) may temporarily be attached or docked onto the retractor (100) by using the clip (505), as shown in FIGS. 8-11. The clip (505) may also be used to attach other secondary devices such as forceps holding gauze or other instruments that the user may prefer to have held out of the way in the vaginal cavity during an examination or procedure.

In some examples, the occluder (131) may comprise a flap (600), as shown in FIGS. 12-15. The flap (600) may temporarily or permanently attached to the distal end of the retractor (100). For example, the flap (600) may temporarily or permanently attached to the distal tip (106). In one example, the flap (600) may be attached to the distal end of the retractor (100) by using a hinge mechanism.

The flap (600) may comprise a flexible material. The flap (600) may be a flat article. In one example, the flap (600) may be a flexible mesh. The mesh may comprise a plastic, a metal, or combinations thereof. The flap (600) may further comprise a porous material, for example, gauze, foam, or combinations thereof.

The flap (600) may be a foldable article. For example, the flap (600) may be folded under the retractor's (100) canopy for storage purposes. For example, before the retractor (100) is deployed in the vagina, the flap (600) may be unfolded to occlude, for example, cervical fluids.

As disclosed above, the central body portion (101), the at least one wing (102 or 103), and the at least one hinge (104 or 105) may form a canopy. In some examples, the canopy may be formed such that the fluid flow through the exterior surface of the canopy, defined by the exterior surfaces of the body (101), wings (102,103) and hinges (104, 105), is substantially blocked.

The central body portion (101) may be convex on the exterior of the retractor (100) and concave on the interior. The central body portion (101) may be of a shape, contour, thickness, angle, radius, and size to hold up the vaginal walls during various procedures.

The wing (102,103) has a proximal end and a distal end. The wing (102,103) also has a top adjacent to the hinge (104,105) and a bottom. The wings (102, 103) may be solid. These wings (102,103) may also be hollow and shell-like to provide a convex exterior and conversely, a generally concave interior to permit visual as well as manual access thereto. The wings (102,103) may be of a shape, contour, thickness, angle, radius, and size to hold up the vaginal walls during various procedures.

The wings (102, 103) may also comprise protruded and/or thinned portions (120, 121) to provide friction and prevent the device (100) from undesirable movement during use. These thinned portions are thinner than the remaining portions of the wing. The protruded and/or thinned portions (120, 121) may protrude from the wings (102, 103) or be etched or carved into the wings. The protruded and/or thinned portions may be anywhere on the wings. The protruded and/or thinned portions may be on the edges of the wings. The protruded and/or thinned portions may comprise various shapes or forms such as grooves, serrations, cross-hatches, bumps, or other morphologies to provide adequate friction with the tissue, while not damaging the tissue or causing discomfort to the patient. In other examples, the top portion of the central body portion (101) may comprise grooves, blunted barbs, or other textures to provide friction and to resist slippage of the retractor (100) within the vaginal cavity. In one example, the wings comprise serrated wing edges. This serrated wing edges may be at the bottom.

An example of the retractor (100) may comprise a so-called "living hinge". In this example, the retractor may be formed as one piece, by using manufacturing techniques such as molding, machining or welding. And the thinned section of the retractor, which is relatively thinner than the central body portion and the wings, forms the living hinge. Thereby, the one-piece retractor can easily flex along the line of the living hinge. A hinge of this type may be capable of many flexures over an extended period of time without the material fatiguing or breaking.

In one example, the width of the living hinge is smaller than the width of the wing (102,103) and/or the central body portion (101). In another example, the living hinge (104, 105) width is substantially smaller than the width of the wing (102,103) and/or the central body portion (101).

The living hinge (104,105) is not the only retractor example that has a canopy wherein the fluid flow through the exterior surface of the canopy is substantially blocked. Other examples are as follows. In one example, the retractor (100) may be formed by substantially reducing the width of the hinge and/or the width of the gap between the central body portion (101) and the wing (102,103). In another example, the wings (102,103) are formed to overlap on the exterior surface of the central body portion (101) or the central body portion (101) is formed to overlap on the exterior surface of the wings (102,103). Yet, in another example, the retractor (100) may further comprise a substantially impermeable membrane that substantially covers the exterior and/or the interior surface of the canopy, or the exterior and/or the interior surface of the gap between the central body portion (101) and the wings (102,103). In yet another example, the retractor (100) may further comprise at least one central body portion (101) and/or at least two wings (102,103) that are entirely or partially flexible such that the wings (102, 103) may be able to move toward or away from each other by bending of the entire structure.

The hinges (104, 105) may comprise the same or different material as the wings (102, 103) and the central body portion (101). The hinges (104, 105) may permit the wings (102, 103) to flex or pivot about the central body portion (101) such that the lower longitudinal wing edges of the retractor may be pivoted open to permit visual and manual access to the interior of a body passage.

The exemplary retractor (100) may also comprise a ratchet mechanism (220). This ratchet mechanism (220) may serve to provide structural support to the wings (102, 103) to counteract the force of the vaginal walls on the wings. This structural support may also prevent the hinges (104, 105) from breaking due to the force of the vaginal walls on the wings (102, 103). The ratchet mechanism (220) may also serve to hold the wings (102, 103) in various positions with respect to each other. For example, the user may desire to have the wings (102, 103) closer to each other during insertion and removal of the retractor (100). Various wing positions may also be desired for different body shapes, sizes, or morphologies.

In some examples, the ratchet mechanism (220) may comprise two ratchet arms (222, 223). In some examples, the ratchet mechanism (220) may prevent the wings (102, 103) from moving toward each other from the force of the vaginal walls, while in other examples the ratchet mechanism (220) may lock together to prevent the wings (102, 103) from moving away from each other due to the configuration of the hinges (104,105). The ratchet arms (222, 223) may attach to three areas of the retractor (100): at the base of each wing's lip (202, 203) and at the retractor limiter (201). The lips (202, 203) may comprise fasteners (255, 256), which may comprise barbed pins that engage the fastener recesses (252, 253) of the ratchet arms (222, 223).

In other examples, the ratchet arms (222, 223) may further attach to the body of the retractor (100) by means of central ratchet hub fastener (230) protruding from the left retractor arm (222), as shown in FIG. 3. The ratchet hub fastener (230) may comprise barbed pins. The ratchet hub fastener (230) may pass through a hole (231) shown in FIG. 3.

The ratchet hub fastener (230) may also fasten to a limiter recess (204) on the proximal side of the retractor limiter (201). The limiter recess (204) may be elongated along its vertical axis in order to allow the fastener pin (230) to slide up and down along the vertical axis of the limiter. This sliding may be necessary as the ratchet arms (222, 223) move away from each other, since in this example the fasteners are fixed to the lips (202, 203).

In other examples, the limiter recess (204) may not be elongated, so that the fastener pin (230) would not move up or down with respect to the retractor limiter (201). Rather, the fastener recesses (252, 253) of the ratchet arms (222, 223) could be elongated so that the fasteners are fixed to the lips (202, 203) and could move along the elongated fastener recesses.

The ratchet arms (222, 223) may also comprise ratchet grasps (262, 263). The ratchet grasps (262, 263) may be useful for spreading the ratchet arms away from, or closer to, each other. The ratchet grasps (262, 263) may also be useful for altering the position of the retractor (100), inserting the retractor, or removing the retractor. The ratchet grasps (262, 263) may further comprise textures, or other protruded and/or thinned portions, in order to increase friction and facilitate gripping by the user. One of the ratchet arms (222, 223) may comprise a ratchet release trigger that comprises a ratchet release trigger handle (243) and a ratchet tooth engager (242). The ratchet tooth engager (242) may latch onto the ratchet teeth (240) of the other ratchet arm. The ratchet tooth engager (242) may release from the ratchet teeth (240) when the user presses the ratchet release trigger handle (243).

A carve-out adjacent to the ratchet teeth may serve as a ratchet limiter engaging slot (246) along which a ratchet limiter stop on the opposing ratchet arm may move as the ratchet arms move relative to each other. This may prevent the distance between the tips of the of the ratchet arms (222, 223) from exceeding three inches. In some examples, the distance may be more than three inches, for instance about four inches. In other examples, it may be 2.5 inches or less.

To stabilize the sliding motion of the main body relative to the ratchet arms, one of the ratchet arms (222, 223) may comprise two pegs (281,282) which are able to travel back and forth within mating grooves (291, 292) integrated within the central body portion (101), thereby effectively restricting rotation of the retractor (100) off axis, swiveling of the central body portion (101) relative to the ratchet arms, and/or buckling of the hinges (104, 105).

The exemplary retractor (100) may also comprise a distal tip (106), which is the first part of the retractor inserted into the body. The distal tip (106) may be thick and wide enough to hold the upper portion of the vaginal walls during various procedures.

The distal end of the distal tip (106) may be round and smooth to provide comfort and minimize damage to the tissue during use. In some examples, the distal tip (106) may comprise only slightly concave, straight, or convex portion such that the open distal tip (106) provides a clear and open view of the cervix. This slightly concave distal tip (106) may resemble a duck-bill in shape, common to existing vaginal speculum designs. In some examples, the distal tip (106) may also comprise grooves, blunted barbs, or other textures to provide friction and to resist slippage of the retractor (100) within the vaginal cavity. In some examples, the distal tip (106) may have a slight curvature suitable to positioning in the vaginal fornices. This positioning of the distal tip (106) in the vaginal fornix may help to ensure that a clear, unobstructed view of the cervix is provided.

The retractor (100) may further comprise a gripping proximal tip (228) at the proximal end. This gripping proximal tip may extend from the proximal end of the central body portion (101). This gripping proximal tip may stick out of the vagina while the rest of the retractor is inserted, and thus allow the user to grab the portion to facilitate altering the position of the retractor (100), inserting the retractor, removing the retractor, or holding the retractor in place. This gripping proximal tip may further comprise textures, or other protruded and/or thinned portions, in order to increase friction and facilitate gripping by the user.

In some examples, the retractor (100) comprises a retractor limiter (201). The limiter (201) may be included in the same molded part as the central body portion (101). The limiter (201) may prevent the retractor (100) from penetrating too far into vagina, and may prevent damage to the cervix, uterus, or other parts of the female patient. The limiter (201) may also have a smooth surface free of surface protrusions or holes in order to prevent painful interaction with the clitoris.

The wings (102, 103) may also comprise lips (202, 203) at their proximal ends. The lips (202, 203) along with the wings (102, 103), the central body portion (101), and the limiter (201) may prevent blood, tissue, or other materials from entering the area where the suturing takes place. The lips (202, 203) may also help to prevent the retractor (100) from penetrating too deeply into the vagina. The lips (202, 203) may also increase stability of the retractor (100), and help to secure its position with respect to the vagina.

The wings (102, 103) may flare outward along a portion of their length. In particular, distance between the opposing wings may be greater toward the end that is deeper the body cavity, and may be narrower toward the opening of the vaginal cavity. Consequently, pressure of the vaginal walls upon the length of the retractor's blades may tend to hold the retractor (100) within the cavity, thereby preventing the retractor (100) from sliding out of the vagina.

In one example, the retractor (100) may further comprise a serrated edge (121), as shown in FIGS. 1-15. The serrated edge (121) may prevent undesired movements, such as slippage, of the retractor (100) when it is placed in the vagina.

In another example, the retractor (100) may further comprise an illumination source. The illumination source may comprise more than one illumination devices.

In other examples, one or all device components forming the illumination source may be located within the retractor limiter (201). In one example, a fiber optic cable or light-guide may direct the light to one or more sites where the light is emitted. The fiber optic cable or light-guide may refract the light for focused or diffuse emission. Yet, in another example, one or all device components forming the illumination source may be located within the canopy formed by the retractor (100). For example, the illumination source may comprise a light-emitting diode wherein the light emitting diode may be located within the retractor canopy. Also, in another example, the whole illumination source is located within the retractor canopy. In such examples, a compact retractor (100) with no illumination source components dangling beyond the other retractor parts may be obtained.

One example the illumination source may comprise a light, such as battery-powered light-emitting diode (LED), located within a light source housing. In some examples, the light source housing may be attached to a cap (not shown) that attaches to the retractor limiter (201). The cap may attach to the limiter by means of a fastener, comprising a pin, which connects to either a ratchet arm (222, 223) or the retractor limiter (201). In some examples, the cap does not have a fastener; rather it may attach by means of an adhesive. In some examples, the light source housing may swivel. In some examples, the user may manually operate the light function externally via a mechanical switch, while in another examples, the light function may be turned on and off automatically. In some examples, the user may control the brightness of the light. In one example, the user may control the brightness of the light by means of a switch, button, or dial.

In other examples, as shown in FIGS. 1-15, the illumination source may comprise a plurality of light emitting components such as light emitting diodes (LEDs) (400) capable of producing sufficient visible light to view the area of interest, a power supply such as coin cell batteries (295) to drive the LED (400), power management components such as resistors, and reed sensor switch (294) to activate the LED (400). The LED (400), resistors, reed switch (294) and power supply batteries (295) may be assembled on a printed circuit board (299), also known as a PCB. Alternatively, the light may be emitted by electroluminescent or chemiluminescent material.

In yet other examples, the illumination source may be automatically turned on and off in conjunction with movement of the ratchet arms (222, 223) away from, and towards, each other, respectively.

Figure 10:
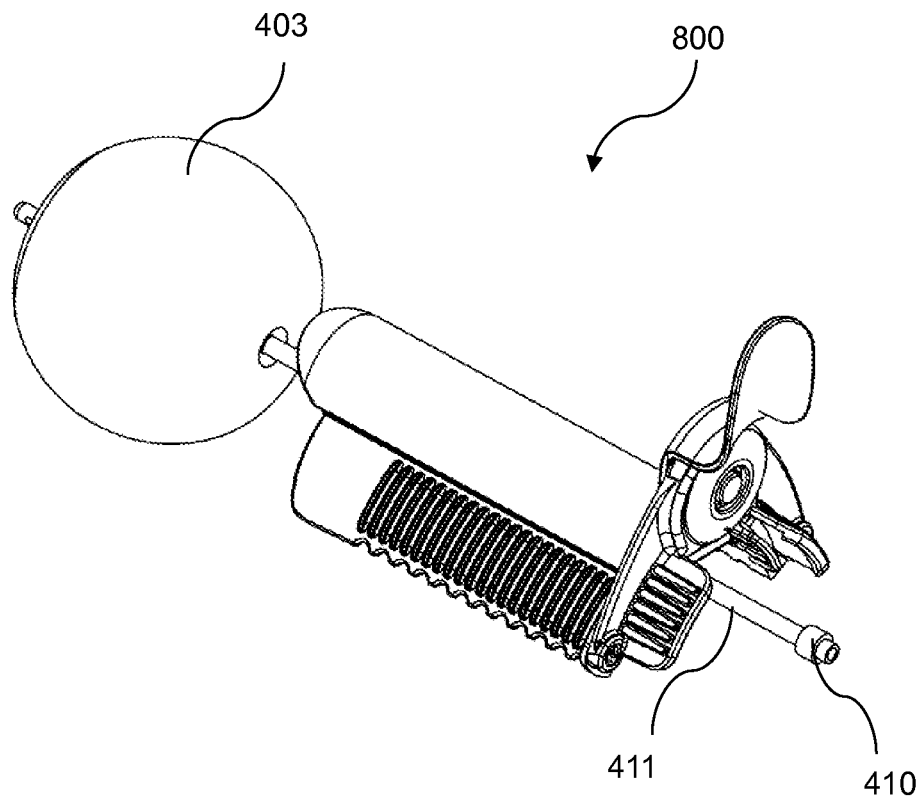
FIG. 10 is an exploded bottom view of the exemplary retractor and a balloon tamponade system attached to the exemplary retractor of FIG. 8.
Figure 11:
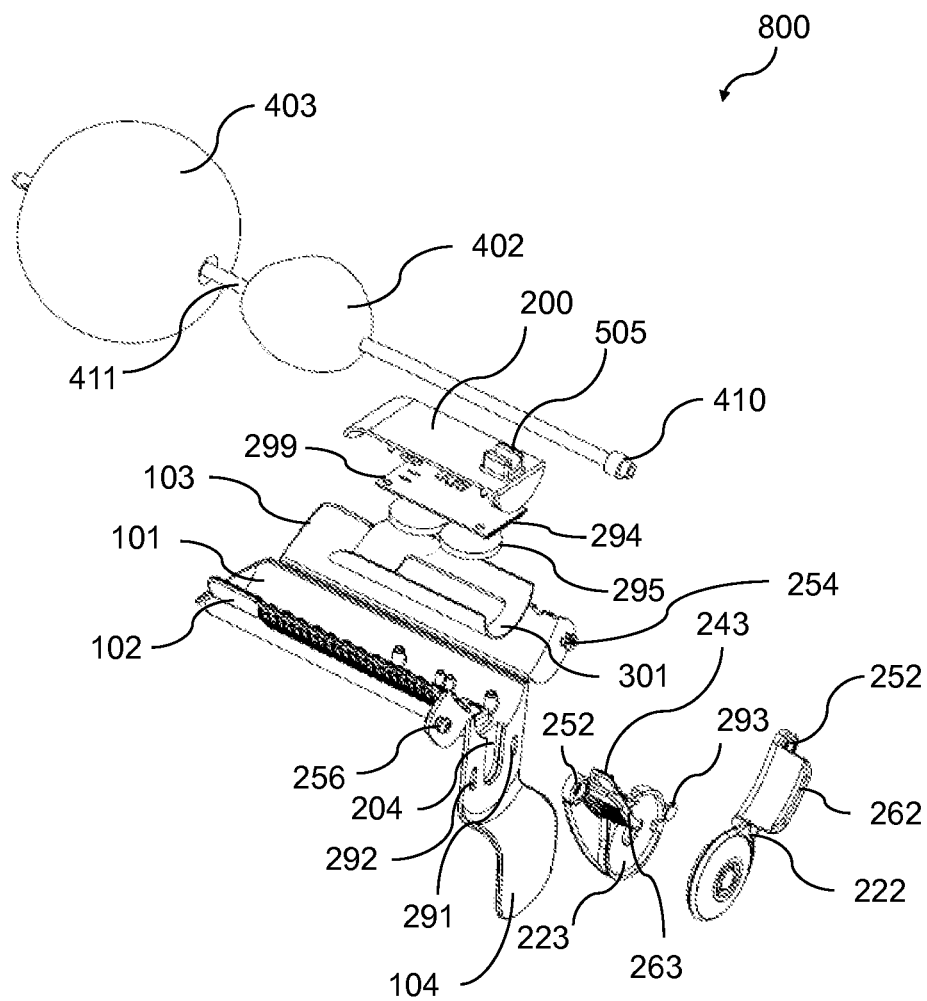
FIG. 11 is an exploded bottom view of the exemplary retractor and a balloon tamponade system unattached to the exemplary retractor of FIG. 8.
Figure 12:
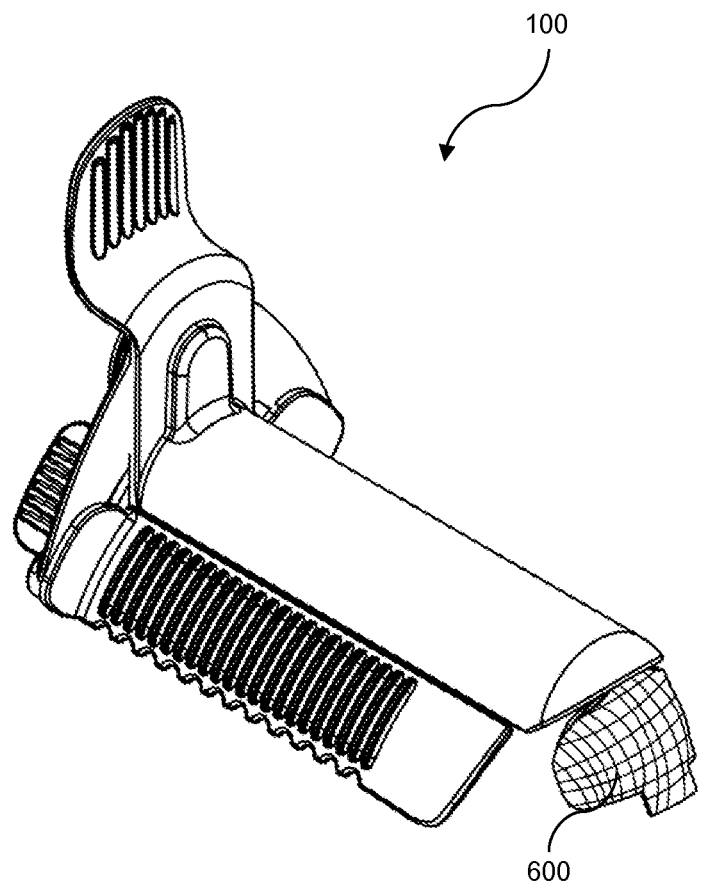
FIG. 12 is an isometric top view of an exemplary retractor comprising a mesh attached to the distal tip.
Figure 13:
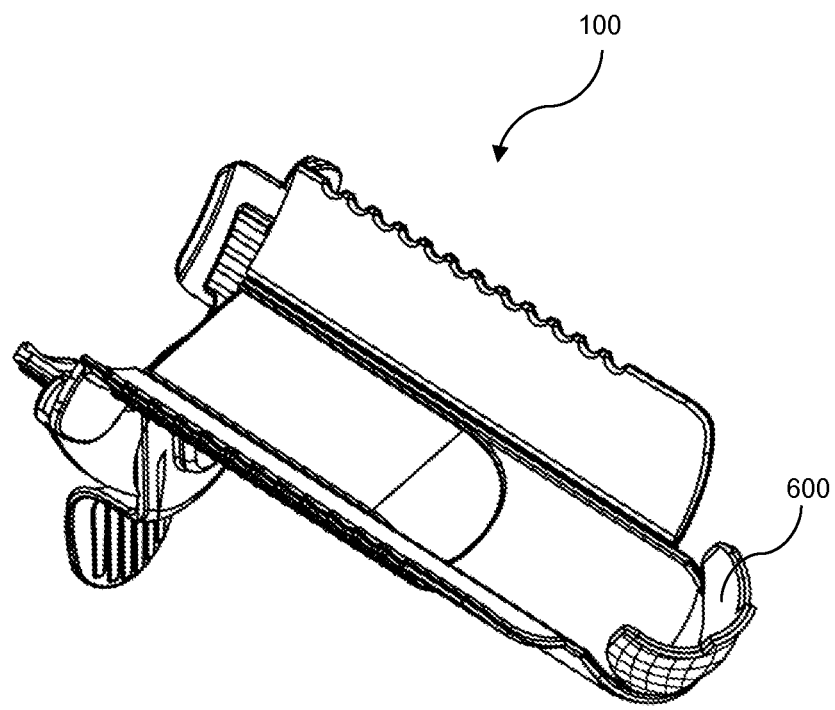
FIG. 13 is an isometric bottom view of the exemplary retractor comprising a mesh attached to the distal tip of FIG. 11.
Figure 14:
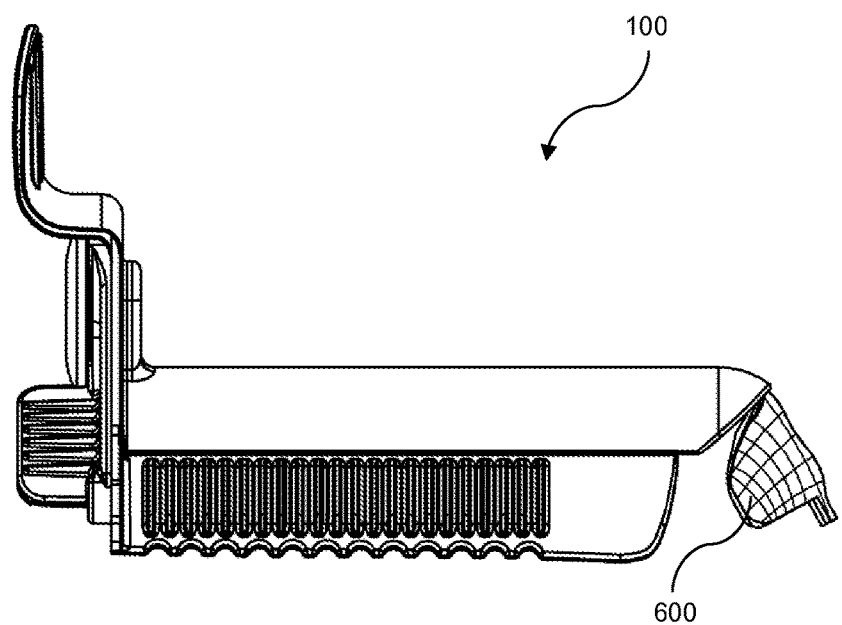
FIG. 14 is an isometric side view of the exemplary retractor comprising a mesh attached to the distal tip of FIG. 11.
Figure 15:
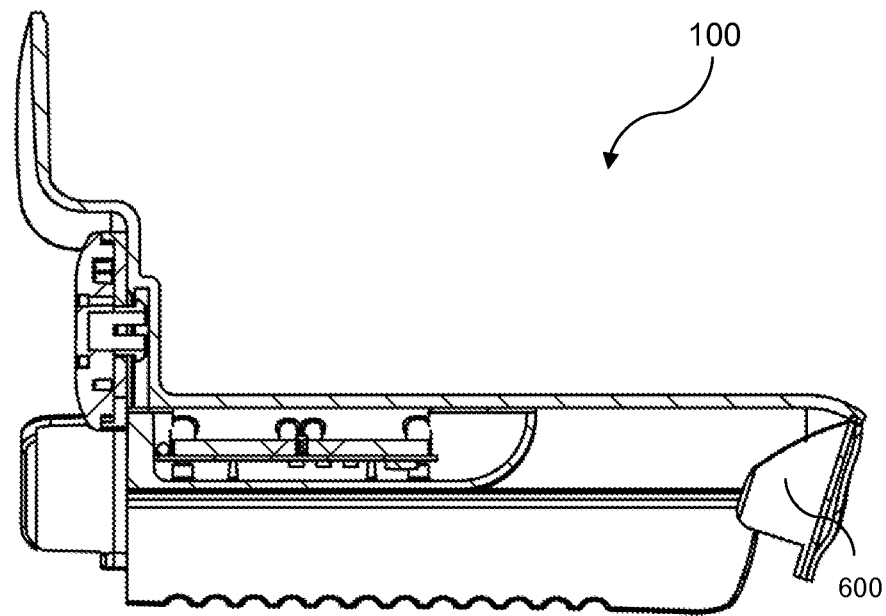
FIG. 15 is a sectional side view of the exemplary retractor comprising a mesh attached to the distal tip of FIG. 11.

In the exploded view of the exemplary retractors shown in FIG. 3 and FIG. 10, the LED may be turned on and off via a reed sensor switch (294). The reed sensor switch (294) may be turned on in the presence of a magnetic field generated by a magnet (293), and may turn off in the absence of the magnetic field generated by the magnet. The reed sensor switch (294) may be sensitive to the position of the magnet (293). The magnet (293) may be installed within a magnet seat (244), which may be located in one of the ratchet arms (222, 223).

The coin cell batteries (295) may be connected using contact wires or directly assembled onto the printed circuit board (299). Alternatively, the electronic components may be brought in contact to complete the circuit without soldering and connected by compression of the assembly packaging.

The LED assembly may be placed onto a plurality of mounting posts (297) on an LED cover (298), which may comprise a translucent material, and assembled into mating features (not shown) located on the underside of the central body portion (101).

A gasket (301) made of rubber or other materials, may be placed between the LED cover (298) and an inner surface of the central body portion (101) to prevent or minimize the ingress of fluids and dirt into the LED assembly. In addition, in the case of leaking power supply batteries, the gasket (301) may prevent chemicals from leaking outside the retractor (100), thereby protecting the user. The gasket (301) may be held in place by mating features in the main body surface, by adhesive, or by other means.

The LED covers (298) and LED assembly may also be mated with the main body via other fastening mechanisms such as screws or epoxy.

The stem may travel in a vertical path inside a slot located with the LED cover (298), thereby making the actuation mechanism hidden from to the user.

In another example, the magnet (293) may be embedded within or attached to one of the ratchet arms (222, 223).

In another example (not shown), the mechanism of turning the light on and off may comprise a mechanical push button switch. The switch may be placed behind the ratchet arms at a location where the arms interact with each other. When the ratchet arms are opened outward and pass over each other, the switch may be triggered, thus completing the electrical circuit and turning on the light.

In another example, the mechanical push button switch may be placed between surfaces of the ratchet arms where the mechanical push switch button may by pressed in the off position when the ratchet arms (222, 223) are closed, thus keeping the light function off. When the ratchet arms (222, 223) are opened outwardly, this may release the switch, thereby turning the switch to the on position, completing the electrical circuit and turning the light function on.

Alternatively, the mechanical push button switch may be accessible to the user to manually turn the light function on or off. The switch may be located on the ratchet arm hub for easy access.

In another example, an optical sensor switch may be used to activate the light function. The switch may be placed in the main body or ratchet arm and between the surfaces thereby occluding the sensor of the switch from ambient light. When the ratchet arms (222, 223) pass over and expose the optical sensor, the switch turns the light function on.

In another example, a breakoff plastic feature may be used to trigger a switch (or an incomplete circuit by a separated wire connection) to turn on the light. In the closed position, one of the ratchet arms (222, 223) may be connected to the switch via a plastic feature or tab. When the ratchet arms (222, 223) are pulled outward to open the wings, this plastic tab could break, consequently activating the switch (or completing the connection between the separated wire) to turn on the light. With this mechanism, the device light function could stay on until the batteries are drained of their power. A variation of this mechanism may use the plastic tab as a cover over the optical sensor switch. On pulling the ratchet arms outwardly, the plastic tab could break and expose the optical sensor, thereby completing the electrical circuit and turning the light on.

In other examples, the device may comprise a plurality of LEDs located at various portions of the interior of the device. For example, the LEDs may be located on or integrated within the interior surfaces of the central body portion (101), the distal tip (106), and/or the wings (102, 103).

In yet other examples, the retractor (100) may comprise only two wings (102,103) and only one central body portion (101). That is, the retractor may not have more than two wings and more than one central body portion.

In some examples, the retractor (100) may be manufactured from a material that may comprise a polymer such as acrylonitrile butadiene styrene (ABS), polyurethane, acetal plastics, or another material known to those skilled in the art that provides both structural rigidity and flexibility. This material may also comprise flexible plastic material such as polyamide sold under the trade name "Nylon," polytetrafluoroethylene sold under the trademark "Teflon". Alternatively, a polypropylene plastic or a high density polyethylene plastic may be used to manufacture the retractor (100). The retractor (100) may be made of a transparent plastic in order to enhance the viewing area. It may also be made of metal. Mixtures or composites of these materials may also be used to manufacture the retractor (100).

The hinge (104,105) may be manufactured from a material that may comprise a polymer. The hinge, for example, may be made from a material comprising polyethylene, polypropylene, nylon, acetal plastics or mixtures thereof. In another example, the hinge material may even be manufactured from a material comprising polyethylene, polypropylene or mixtures thereof.

The retractor (100) may be sterilizable by ethylene oxide, gamma radiation or other process known to those skilled in the art. It may be disposable or reprocessable. Also, the retractor (100) may be made of different sizes and/or thicknesses to accommodate different ages and sizes of patients. The retractor (100) may be coated with a material to facilitate inspection and movement. For example, a lubricant can be used to coat the retractor (100) to facilitate insertion and retrieval.

In some examples, a significant portion of the retractor (100) may be formed from a single continuous material. That is, the retractor is formed from only one component. In these examples, the retractor may be manufactured by molding. For example, the central body portion (101), wings (102, 103), and distal tip (106) may be injection molded to form a single component. An exemplary material for injection molding may be polypropylene.

In some examples, the retractor (100) may be sized to fit vaginas of different size ranges. In other examples, the retractor (100) may be sized to fit larger vaginas. In some examples, the retractor's dimensions and contours may accommodate the excess tissue of overweight and obese patients. These variations may consist of differences in any of a variety of dimensions of the retractor and its features, such as the overall length of the retractor (100); the length and/or width of the central body portion (101); and/or the span, length, shape, and/or morphology of the wings (102, 103).

Any combination of features and/or embodiments of the retractor (100) and the system (800) disclosed above is within the scope of this disclosure. For example, the system may comprise a retractor; wherein the retractor does not have more than two wings, does not have more than one central body portion, at least two hinges, and an occluder; and wherein the occluder comprises a porous material; and wherein the occluder is movable with respect to the central body portion. For example, the system may comprise a retractor; wherein the retractor does not have more than two wings, does not have more than one central body portion, at least two hinges, and an occluder; and wherein the system further comprises a secondary device that is temporarily attachable to the retractor; and wherein the retractor further comprises a docking port to securely attach the secondary device to the retractor. For example, the system may comprise a retractor; wherein the retractor does not have more than two wings, does not have more than one central body portion, at least two hinges, and an occluder; and wherein the system further comprises a secondary device that is temporarily attachable to the retractor; and wherein the retractor further comprises a docking port to securely attach the secondary device to the retractor; and wherein the secondary device comprises a double balloon tamponade system, and wherein the one balloon of the double balloon tamponade system may function as a uterine tamponade balloon, and wherein the other balloon of the double balloon tamponade system may function as a vaginal tamponade balloon.

The retractor (100) may be used in various procedures, including episiotomy repair, repair of vaginal lacerations, and visualization during checkups. For example, the ratchet mechanism may be adjusted to hold the wings (102, 103) in various positions with respect to each other. For example, the user may desire to have the wings (102, 103) closer to each other during insertion and removal of the retractor (100), while keeping the wings (102, 103) farther apart from each other to maximize the viewing and working fields during procedures. Various positions may also be desired for different body shapes, sizes, or morphologies. The position of the wings may be changed during procedures using the ratchet mechanism.

The retractor (100) may be used for improved visualization, access, and repair in various procedures, including, but not limited to: obstetrical/gynecological procedures: vaginal inspection; perineal inspection; vaginal wound repair; perineal wound repair; episiotomy repair; female pelvic exam; pap smear; cervical biopsy; vaginal/pelvic reconstruction; urological procedures; colorectal, general, or other surgery; the retractor (100) may be turned upside-down, for example, for female urologic procedures; access to the cervix (or uterus via cervix); IUD insertion, removal, or adjustment; and dilatation & curettage (dilatation of cervix and curettage of uterus). The retractor (100) may also be used as a speculum for colposcopy.

A vaginal laceration typically has its apex nearer the cervix and become wider toward the introitus. In using the retractor (100), the user may begin suturing a vaginal laceration with the retractor (100) deployed in the vagina in its open position, with the retractor (100)'s wings (102, 103) spread apart. The suture is typically started at the apex of a tear deeper in the vagina, nearer the vaginal vault or cervix. While proceeding to suture and moving toward the introitus, where the tear is typically wider than at its deeper apex, the user may adjust the retractor (100) to a more closed position, with its wings (102, 103) closer to each other. This may ease the approximation of tissue from opposing sides of the laceration. Intermittent, slight closing of the retractor (100) as the suturing is performed may allow the user to achieve the appropriate degree of retraction throughout the run of the suture, until the suturing is complete.

The retractor (100) and the system (800) may be used in a variety of medical and surgical procedures including vaginal and perineal wound repair, episiotomy repair, pelvic floor repair and/or reconstruction, and/or cosmetic gynecology procedures.

The instant disclosure also relates to a method of using the retractor (100) or the system (800). In one example, the method of using the retractor (100) or the system (800) may comprise providing the system or the retractor, deploying the retractor into the vagina, spreading the at least two wings apart, and occluding the cervix to reduce the flow of the bodily fluids into the vagina. In another example, such method may further comprise providing the system or the retractor that further comprises a movable occluder (131) and moving the occluder towards the cervix to reduce the flow of the bodily fluids into the vagina. Yet in another example, the method may further comprise repositioning the retractor by rotating the retractor within the vagina. Still in another example, the method further comprises repositioning the retractor by removing the retractor from the vagina, and then re-deploying the retractor within the vagina. Also, the method further comprises closing the wings and then removing the retractor from the vagina.

In another exemplary method, the occluder (131) may further comprise a balloon tamponade system, wherein the balloon tamponade system further comprises a catheter, wherein the retractor further comprises a docking port to securely and detachably attach the balloon tamponade system to the retractor. This method further comprises providing the balloon tamponade system, attaching the balloon tamponade system to the retractor, and then deploying the retractor into the vagina.

Yet in another exemplary method, the vaginal laceration may be sutured by using the system (800) or the retractor (100) as follows. The methods disclosed above may further comprise suturing the laceration starting at the apex of the laceration deeper in the vagina, continuing with the suturing towards introitus, and gradually closing the wings while the continuing with the suturing.

Any combination of methods and method features or steps disclosed above that utilize the retractor (100) and the system (800) disclosed above is within the scope of this disclosure.

The previous description of examples is provided to enable any person skilled in the art to make or use the retractors and speculums. Various modifications to these examples will be readily apparent to those skilled in the art, and the generic principles defined herein may be applied to other examples without departing from the spirit or scope of the retractors and speculums. Thus, the retractors and speculums are not intended to be limited to the examples shown herein but are to be accorded the widest scope consistent with the principles and novel features disclosed herein.

The components, steps, features, objects, benefits and advantages which have been discussed are merely illustrative. None of them, nor the discussions relating to them, are intended to limit the scope of protection in any way. Numerous other examples are also contemplated. These include examples which have fewer, additional, and/or different components, steps, features, objects, benefits and advantages. These also include examples in which the components and/or steps are arranged and/or ordered differently.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

Nothing which has been stated or illustrated is intended or should be interpreted to cause a dedication of any component, step, feature, object, benefit, advantage, or equivalent to the public, regardless of whether it is recited in the claims.

We claim:

1. A system, comprising
a minimally obstructive retractor having a proximal end, a distal end, an exterior surface, and an interior surface, comprising:
a central body portion,
at least two wings,
two hinges, each configured to affix a different one of the at least two wings to the central body portion, and
a rachet mechanism that releasably locks the wings in an open position; and
an occluder affixed to the retractor,
wherein the wings are rotatable about the hinges when moving from a closed to an open position;
wherein the at least one occluder is positioned underneath the canopy, at the distal end of the retractor, beyond the distal end of the retractor, or a combination thereof;
wherein the wings, the hinges, and the central body portion form a canopy that creates and only partially surrounds an interior space that is not surrounded by any other portion of the retractor when the wings are in the open position;
wherein no portion of the retractor obstructs any portion of the interior space formed by the canopy when the wings are in the open position,
wherein the occluder is configured to at least partially occlude bodily fluid from entering into a volume formed by the at least two wings when spread apart and by tissue surrounding the spread wings, and/or at least to reduce bleeding of a uterus, cervix, and/or vagina.

2. The system of claim 1, wherein the occluder is configured to occlude the bodily fluids by forming a barrier that is partially impermeable to the bodily fluid.

3. The system of claim 1, wherein the occluder is configured to occlude the bodily fluids by forming a barrier that is substantially impermeable to the bodily fluid.

4. The system of claim 1, wherein the occluder comprises a material that is configured to absorb the bodily fluid.

5. The system of claim 1, wherein the occluder comprises a porous material.

6. The system of claim 1, wherein the occluder is movable with respect to the central body portion.

7. The system of claim 1, wherein the retractor further comprises a distal tip and wherein the occluder is attached to the distal tip.

8. The system of claim 1, wherein the occluder comprises an inflatable article.

9. The system of claim 8, wherein the inflatable article does not have more than one balloon.

10. The system of claim 8, wherein the inflatable article does not have more than two balloons.

11. The system of claim 8, wherein the inflatable article is inflatable by a fluid.

12. The system of claim 1, wherein the occluder comprises a single balloon tamponade system, comprising a single balloon.

13. The system of claim 12, wherein the retractor further comprises a docking port to securely and detachably attach the single balloon tamponade system to the retractor.

14. The system of claim 12, wherein the single balloon is positioned at the distal end of the retractor.

15. The system of claim 12, wherein the single balloon is positioned underneath the canopy.

16. The system of claim 12, wherein the single balloon is positioned at the distal end of the retractor and/or beyond the distal end of the retractor.

17. The system of claim 1, wherein the occluder comprises a double balloon tamponade system, comprising two balloons.

18. The system of claim 17, wherein the retractor further comprises a docking port to securely and detachably attach the double balloon tamponade system to the retractor.

19. The system of claim 17, wherein at least one balloon is positioned underneath the canopy.

20. The system of claim 17, wherein at least one balloon is positioned at the distal end of the retractor and/or beyond the distal end of the retractor.

21. The system of claim 17, wherein one balloon is positioned underneath the canopy; and the other balloon is positioned at the distal end of the retractor and/or beyond the distal end of the retractor.

22. The system of claim 1, wherein the system further comprises a secondary device that is temporarily attachable to the retractor.

23. The system of claim 1, wherein the retractor does not have more than two wings and does not have more than one central body portion.

24. The system of claim 23, wherein the occluder comprises a porous material, and wherein the occluder is movable with respect to the central body portion.

25. The system of claim 23, wherein the system further comprises a secondary device that is detachably attached to the retractor, and wherein the retractor further comprises a docking port that securely attaches the secondary device to the retractor.

26. The system of claim 23, wherein the occluder comprises a double balloon tamponade system, comprising two balloons; and wherein one balloon of the double balloon tamponade system functions as a uterine tamponade balloon, and wherein the other balloon of the double balloon tamponade system functions as a vaginal tamponade balloon.

27. The system of claim 1, wherein the ratchet mechanism comprises at least one arm that is affixed to an interior surface of at least one of the wings.

28. The system of claim 27, wherein the retractor further comprises two mating grooves, which are integrated within the ratchet mechanism, and two pegs; and wherein the two mating grooves and the two pegs are configured to effectively restrict rotation of the retractor off axis.

29. The system of claim 28, wherein the retractor further comprises a retractor limiter at the proximal end.

30. The system of claim 29, wherein the retractor limiter further comprises a limiter recess.

31. The system of claim 30, wherein the occluder comprises a single balloon tamponade system, comprising a single balloon.

32. The system of claim 31, wherein the single balloon is positioned at the distal end of the retractor.

33. The system of claim 31, wherein the single balloon is positioned beyond the distal end of the retractor.

34. The system of claim 31, wherein the retractor further comprises a docking port to securely and detachably attach the single balloon tamponade system to the retractor.

35. The system of claim 30, wherein the occluder comprises a double balloon tamponade system, comprising two balloons.

36. The system of claim 35, wherein one balloon is positioned underneath the canopy; and the other balloon is positioned at the distal end of the retractor, beyond the distal end of the retractor, or a combination thereof.

37. The system of claim 35, wherein one balloon is positioned underneath the canopy; and the other balloon is positioned beyond the distal end of the retractor.

38. The system of claim 35, wherein the retractor further comprises a docking port to securely and detachably attach the double balloon tamponade system to the retractor.

39. The system of claim 35, wherein one balloon of the double balloon tamponade system functions as a uterine tamponade balloon, and wherein the other balloon of the double balloon tamponade system functions as a vaginal tamponade balloon.

40. The system of claim 1, wherein the system comprises a lever, rod, or switch that allows a user to move the occluder independently of the central body portion, wings, and hinges, after the retractor is inserted into the vagina.

41. A system, comprising:
a vaginal retractor, comprising:
a central body portion;
at least two wings;
two hinges that affix a different one of the at least two wings to the central body portion; and
an occluder attached to a component of the system, wherein the occluder is an occluder that is configured to occlude bodily fluid from entering into a volume formed by the at least two wings when spread apart and by tissue surrounding the spread wings; and
a lever, rod, or switch that allows a user to move the occluder independently of the central body portion, wings, and hinges, after the retractor is inserted into a vagina.

* * * * *